(12) United States Patent
Barber

(10) Patent No.: US 7,325,708 B2
(45) Date of Patent: Feb. 5, 2008

(54) OCULAR POSITIONING DROPLET DISPENSING DEVICE WITH A RECESSED DISPENSING ORIFICE

(76) Inventor: Rory Barber, 5335 Pleasant Hill Dr., Fenton, MI (US) 48430

( * ) Notice: Subject to any disclaimer, the term of this patent is extended or adjusted under 35 U.S.C. 154(b) by 468 days.

(21) Appl. No.: 11/035,862

(22) Filed: Jan. 14, 2005

(65) Prior Publication Data

US 2006/0157516 A1    Jul. 20, 2006

(51) Int. Cl.
*B65D 47/18* (2006.01)

(52) U.S. Cl. .................. 222/420; 222/546; 222/556; 222/562; 604/294; 604/295; 604/300; 604/302

(58) Field of Classification Search ........ 222/420–422, 222/556–557, 562–563, 546, 186; 604/294–296, 604/300–303
See application file for complete search history.

(56) References Cited

U.S. PATENT DOCUMENTS

| | | | | |
|---|---|---|---|---|
| 3,446,209 A | * | 5/1969 | August ..................... 604/302 |
| 3,872,866 A | * | 3/1975 | Lelicoff ..................... 604/302 |
| 3,934,590 A | | 1/1976 | Campagna et al. ......... 128/233 |
| 4,605,398 A | * | 8/1986 | Herrick ..................... 604/300 |
| 4,915,268 A | * | 4/1990 | Lay et al. .................. 222/498 |
| 5,178,613 A | | 1/1993 | Gibilisco ................... 604/294 |
| 5,181,634 A | | 1/1993 | Gibilisco ................... 222/212 |
| 5,207,657 A | * | 5/1993 | Gibilisco ................... 604/295 |
| 5,221,017 A | * | 6/1993 | Cistone et al. ............. 215/235 |
| 5,246,145 A | * | 9/1993 | Leoncavallo et al. .. 222/153.14 |
| 5,366,448 A | * | 11/1994 | Basilice et al. ............ 604/290 |
| 5,578,019 A | * | 11/1996 | Feldman ................... 604/295 |
| 5,702,033 A | * | 12/1997 | Beaver ...................... 222/94 |
| 5,848,999 A | * | 12/1998 | Basilice et al. ............ 604/300 |
| 5,902,292 A | | 5/1999 | Feldman ................... 604/295 |
| 6,010,488 A | | 1/2000 | Deas ........................ 604/295 |
| 6,090,086 A | * | 7/2000 | Bolden ..................... 604/302 |

* cited by examiner

*Primary Examiner*—Frederick C. Nicolas
(74) *Attorney, Agent, or Firm*—Brian S. Steinberger; Law Offices of Brian S. Steinberger, P.A.

(57) ABSTRACT

An ocular positioning device threadably attached to a standard soft sided squeeze bottle of ophthalmic fluid. The device consists of two parts, an attaching mechanism and a sealing mechanism, connected by a hinge with motion limited to ninety degrees of arc. The sealing mechanism is fitted with a nose bridge saddle designed to rest on the bridge of the users nose and to align the discharge nozzle with the central portion of the ocular opening of either of the users eyes when the attaching hinge is in the fully open position. The sealing mechanism is also fitted with a manually operated latch to maintain the sealing mechanism in the closed and sealed condition to prevent leakage when not in use.

9 Claims, 2 Drawing Sheets

OCULAR POSITIONING DROPLET DISPENSING DEVICE WITH A RECESSED DISPENSING ORIFICE

BACKGROUND

1. Field of Invention

This invention relates to eye drop dispensers and more specifically to eye drop dispensers having recessed dispensing orifice and alignment attachment to position the dispensing orifice over the approximate center of the ocular opening.

2. Description of Prior Art

Liquid eye drops are commonly used to introduce over the counter and prescription medication into the eyes of human patients. The most common container in which these eye drops are supplied is simply a flexible plastic bottle having a tapered dropper. It has been recognized that a flexible bottle with a tapered dropper does not provide optimum means for administering drops into the eye. A significant problem with previous dispensing devices used for dispensing ophthalmic solutions is contamination of the dropper nozzle by inadvertent contact with septic surfaces such as fingertips and facial surfaces. This contact also can clog the dispensing orifice making it impossible to dispense further drops. Contamination of the dispensing orifice can then result in microbial contamination of the solution remaining in the dropper bottle and the transfer of this contamination to either or both eyes.

Some devices have been reported which serve to prevent contact of the dispensing orifice but were designed primarily to aid in the in positioning the dispensing orifice properly. See for example U.S. Pat. Nos. 5,578,019; 5,902,292; 6,010,488; 6,090,086. These devices generally comprise members which rests on the patients face serving to retract the lower eyelid and to prevent unwanted blinking so that drops from the dispensing orifice will enter the eye. Little or no mention is made of prevention of contamination of the of the dispensing orifice by contact with a septic surface or means to align the dispensing orifice with the proper area of the eye for receiving the medication. U.S. Pat. Nos. 5,178,613; 5,181,634; 5,207,657 teach the protection of the dispensing orifice but no mention is made of means to align the dispensing orifice with the proper area of the eye. U.S. Pat. Nos. 6,010,488 and 6,090,086 both teach the means to retract the lower eyelid but do not teach protection of the dispensing orifice from contact with a septic surface or the alignment of the dispensing orifice. U.S. Pat. No. 3,934,590 teaches alignment of the dispensing orifice with the correct portion of the eye but the tip of the dispensing orifice is exposed to contamination prior to and after dispensing the medication and prior to replacing the sealing cap. Since the eye drops may be used several times a day and over long periods of time, it is often necessary to carry the dispenser in a purse or a pocket, the size and configuration of the ocular positioning droplet dispensing device of U.S. Pat. No. 3,934,590 would make carriage in a purse or pocket difficult.

SUMMARY OF INVENTION

The present invention employs a recessed dispensing orifice to prevent the inadvertent contact of the dispensing orifice with septic surface that may clog the dispensing orifice or contaminate the medication in the eye drop bottle. Another object of the present invention is to provide an ocular positioning droplet dispensing device of the character described which will be handled and positioned by only one hand of the user leaving the other hand free to assist in holding open the eye being treated.

Another further object of the present invention is to provide an ocular positioning droplet dispensing device of the character above with minimal training or experience can be quickly and easily positioned over the eye to be treated and with ease and facility be rotated from one eye to the other.

Still another object of the present invention is to provide an ophthalmic droplet dispensing device of the character described that is affixed to the droplet bottle at all times and is of sufficiently small dimensions that it may be conveniently carried in a pocket or purse.

The invention possesses other objects and features of advantage, some of which of the foregoing will be set fourth in the following description of the preferred form of the invention which is illustrated in the drawing accompanying and forming part of this specification. It is to be understood, however, that variations in the showing made by said drawings and description may be adopted within the scope of the invention as set fourth in the claims.

DETAILED DESCRIPTIONED OF INVENTION

Figure 1:
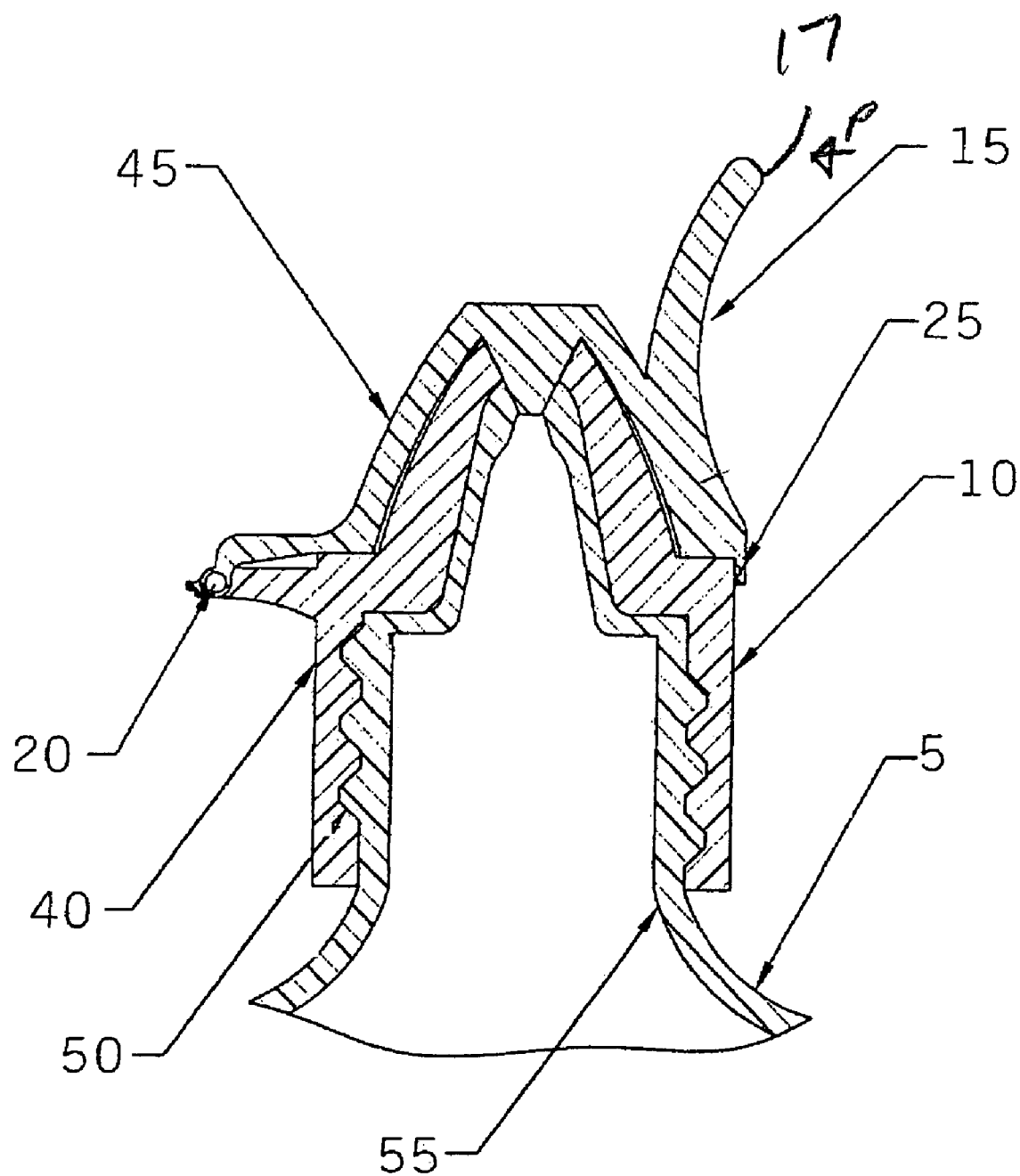
FIG. 1 is a longitudinal, cross-sectional, view of the ocular positioning droplet dispensing device constructed in accordance with the present invention and is shown in the closed position, attached to a sectioned portion of the droplet bottle.
Figure 2:
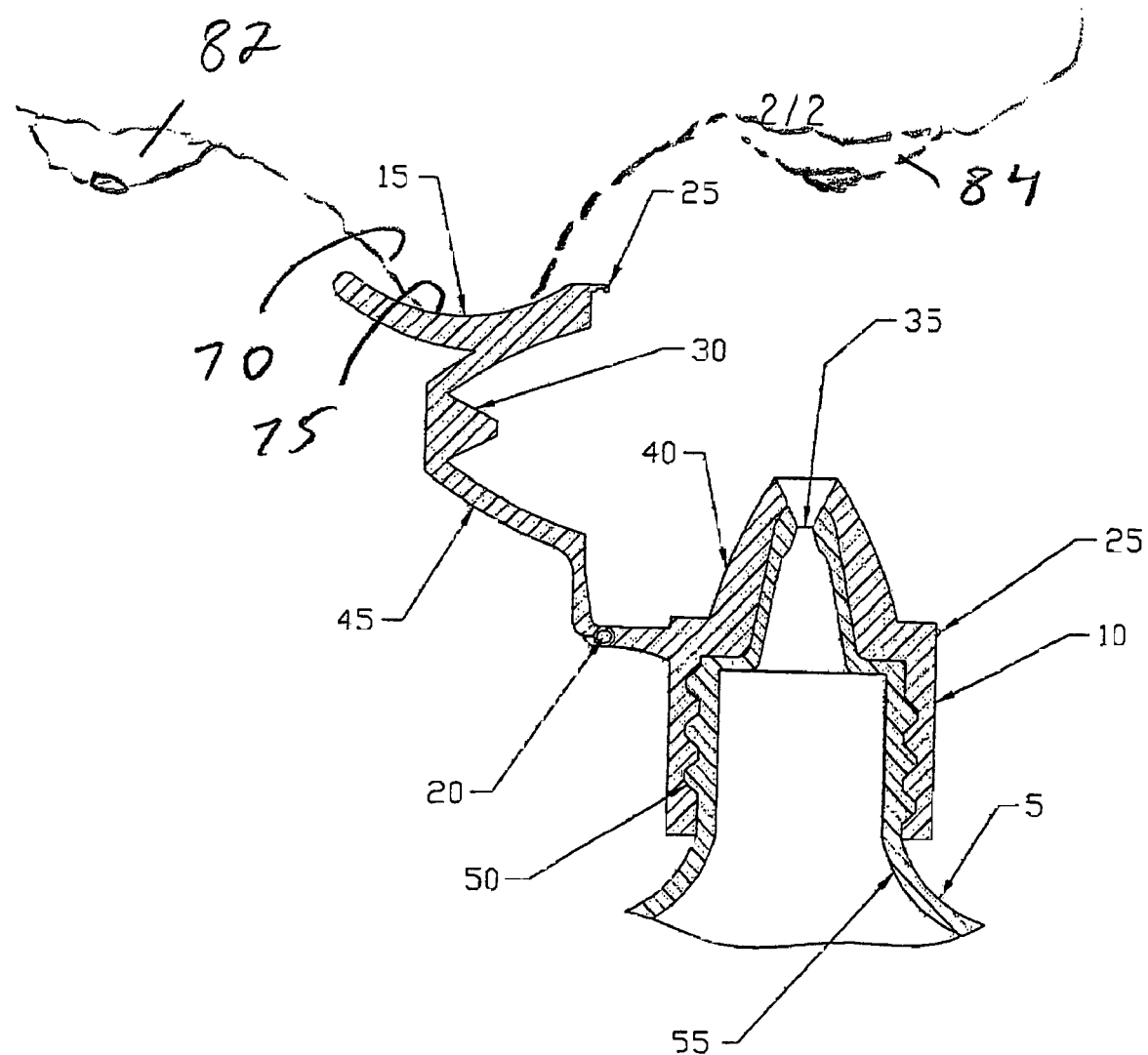
FIG. 2 is a longitudinal, cross-sectional, view of the ocular positioning droplet dispensing device constructed in accordance with the present invention and is shown in the open position, attached to a sectioned portion of the droplet bottle.

The ocular positioning droplet dispensing device 10 of the present invention is intended for delivery of sterile fluids such as ophthalmic fluids intended for administration to the eye, comprises briefly two parts. Attaching mechanism 40 having female threads 50 for attaching the droplet dispensing device 10 to the droplet bottle 5 and providing a recessed dispensing orifice 35 that protects the contents of the droplet bottle 5 from contact with septic surfaces. The sealing section 45 of the droplet dispensing device 10 is attached to attaching mechanism 40 by a limited motion hinge 20, which limits the motion of the sealing section 45 from the closed position as seen in FIG. 1 to the full open position as seen in FIG. 2. The flexible latch 25 serves to hold the sealing plug 30 in the closed position to prevent leakage of the ophthalmic fluid from the droplet bottle 5. The sealing section 45 of the droplet dispensing device 10 is fitted with a positioning saddle 15 being formed for mounting on the bridge of the nose of the user. When the positioning saddle 15 is so mounted and the hinge 20 is in the full open position the recessed dispensing orifice 35 is positioned over the central portion of the ocular opening.

Eye drops, both prescription and non-prescription, are almost universally dispensed in a soft sided squeeze bottle 5. The Standard droplet bottle 5 is formed with a reduced, substantially cylindrical neck 55 which is fitted with a dispensing orifice 35. A cap is usually threadably attached to neck 55 to provide a demountable closure for the dispensing orifice 35.

To use the device the cap is removed and discarded. The droplet dispensing device 10 is thread ably attached to the droplet bottle 5, thereby replacing the sealing demountable cap. The latch 25 is released by pressing against the upper edge of the saddle 15 in the direction of arrow P, and the sealing section 45 of the droplet dispensing device 10 is moved to the open position as seen in figure 2. The positioning saddle 15 is then positioned in the bridge 75 of the user's nose 70 directly between the eyes 82, 84 of the person receiving the ophthalmic liquid thereby aligning the dispensing orifice with the central area of the ocular opening of the intended recipient. The required dose of ophthalmic fluid is then administered by squeezing bottle 5 over one eye 84. If ophthalmic fluid is required in both eyes the droplet dispensing device 10 and droplet bottle 5 assemblies can be rotated 180 degrees to position the dispensing orifice 35 over the other eye. The positioning, dispensing and rotation operations are accomplished with one hand leaving the other hand free to prevent the closing of the eye during dispensing of the ophthalmic fluid. The description given above presents an improved apparatus for dispensing ophthalmic fluids, it will be appreciated that the positioning saddle within this invention enables the ophthalmic fluid dispensing applicator to be safely and accurately used by any mature individual, regardless of the size or shape of their face. Moreover, the closure system enables the user to dispense ophthalmic fluids without compromising sterility within the container.

While a preferred embodiment is for the foregoing has been shown and described, it will be understood that the description is not intended to limit the disclosures but rather is intended to cover all modifications and alternate methods falling within the spirit of and scope of the invention as defined in the appended claims.

What is claimed is:

1. An ocular positioning device for a standard soft sided squeeze bottle of ophthalmic fluid having a reduced externally threaded droplet discharge nozzle comprising:
    a dispensing mechanism having a dispensing orifice for threadably attaching to the externally threaded droplet discharge nozzle;
    a cap sealing section directly attached to said dispensing mechanism by a limited motion hinges, and having a sealing plug dimensioned to slidably enter and seal said dispensing orifice and the discharge nozzles;
    a positioning saddle having one side secured directly to said cap sealing section and having an opposite free side with a concavely notched surface, wherein the concavely notched surface on the opposite free side of the saddle is adapted to seat upon a bridge of a user's nose and to position said droplet discharge nozzle in a fixed vertical alignment raised above and separated from an eye of the user's eye when the droplet dispensing device is used; and
    a flexible manually operable latch mechanism on the cap sealing section to securely hold the sealing plug in sealing relation with the said discharge nozzle when said droplet dispensing device is not in use.

2. The device of claim 1, said limited motion hinge being limited to an arc of approximately 90 degrees.

3. The device of claim 1, wherein the dispensing mechanism and cap sealing mechanism are each dome shaped, so that the cap sealing mechanism fits over and about the dispensing mechanism, and wherein the sealing plug includes a downwardly projecting member that is located inside of the cap sealing member.

4. The device of claim 2, wherein the saddle includes an upper exposed edge that allows the user to press against to open the droplet dispensing device to be used.

5. The device of claim 3, wherein the saddle is fixably attached on one side of the cap sealing mechanism, and the hinge is fixably attached to an opposite side of the cap sealing mechanism.

6. An ocular positioning droplet dispensing device, comprising in combination:
    a squeezable bottle of ophthalmic fluid having a narrow droplet discharge nozzle with a dispensing orifice;
    a cap sealing member having a closed position for fitting over and plugging the dispensing orifice of the narrow droplet discharge nozzle, the cap sealing member having an open position;
    a saddle member having one side fixably attached to one side of the cap sealing member, the saddle member having an exposed free side with concave surface which is opposite to the one side, the saddle member having an upper edge that when pressed moves the cap sealing member to the open position; and
    a hinge for attaching a second side of the cap sealing member to the discharge nozzle neck of the bottle, the second side of the cap sealing member being opposite to the first side of the cap sealing member, the hinge having a closed position when the cap sealing member is fitting over and plugging the dispensing orifice of the discharge nozzle, the hinge having an open extended position for allowing the concave surface free side adaptable to be positioned on a bridge of a nose of a user, and allow the dispensing orifice of the discharge nozzle to be positioned in a fixed state raised above and separated from one eye of the user.

7. The ocular positioning droplet dispensing device of claim 6, wherein the cap sealing member includes:
    a downwardly extending plug that fits into and seals the dispensing orifice of the discharge nozzle when the cap sealing member is in the closed position, and the plug is oriented perpendicular to and spaced apart from the dispensing orifice when the cap sealing member is in the open position.

8. The ocular positioning droplet dispensing device of claim 7, wherein the open extended position of the hinge is limited to an arc of approximately 90 from the closed position of the hinge.

9. The ocular positioning droplet dispensing device of claim 8, further comprising:
    a dome shaped dispensing attachment with a dispensing orifice, the dispensing attachment having internal threads for threadably attaching to exterior threads on the narrow droplet discharge nozzle, the dispensing orifice of the dispensing attachment being aligned with the dispensing orifice of the discharge nozzle, the hinge being directly attached to one side of the dome shaped dispensing attachment.

* * * * *